United States Patent [19]

Linn et al.

[11] Patent Number: 4,579,864

[45] Date of Patent: Apr. 1, 1986

[54] AVERMECTIN AND MILBEMYCIN 13-KETO, 13-IMINO AND 13-AMINO DERIVATIVES

[75] Inventors: Bruce O. Linn, Bridgewater; Helmut H. Mrozik, Matawan, both of N.J.

[73] Assignee: Merck & Co., Inc., Rahway, N.J.

[21] Appl. No.: 619,238

[22] Filed: Jun. 11, 1984

[51] Int. Cl.$^4$ .................. A61K 31/365; C07D 493/20
[52] U.S. Cl. .................................. 514/450; 514/409; 548/525; 549/264
[58] Field of Search ........................ 424/279; 548/525; 549/264; 514/450, 409

[56] References Cited

U.S. PATENT DOCUMENTS

| | | | |
|---|---|---|---|
| 3,950,360 | 4/1976 | Aoki et al. | 536/17 A |
| 4,134,973 | 1/1979 | Fisher et al. | 536/4 |
| 4,171,314 | 10/1979 | Chabala et al. | 536/17 A |
| 4,173,571 | 11/1979 | Chabala et al. | 536/17 A |
| 4,199,569 | 4/1980 | Chabala et al. | 536/9 |
| 4,201,861 | 5/1980 | Mrozik et al. | 536/17 A |
| 4,206,205 | 6/1980 | Mrozik et al. | 536/17 A |
| 4,289,760 | 9/1981 | Mrozik et al. | 549/264 |
| 4,310,519 | 1/1982 | Albers-Schonberg et al. | 435/76 |

OTHER PUBLICATIONS

*Tetrahedron Letters* 24 5333–5336, (1983).

*Primary Examiner*—Jane T. Fan
*Attorney, Agent, or Firm*—David L. Rose; Michael C. Sudol, Jr.; Mario A. Monaco

[57] ABSTRACT

There are disclosed novel avermectin and milbemycin compounds wherein the 13-position is oxidized to a keto function. The 13-keto derivatives are prepared from the 13-hydroxy compounds by oxidizing the 13-position with a suitable oxidizing agent. The avermectin and milbemycin 13-keto derivatives are active in their own right and also serve as intermediates in the preparation of 13-imino and 13-amino derivatives. The 13-keto, imino and amino compounds have utility as anti-parasitic agents and compositions for that use are also disclosed. The compounds are also highly potent insecticides against agricultural pests.

13 Claims, No Drawings

AVERMECTIN AND MILBEMYCIN 13-KETO, 13-IMINO AND 13-AMINO DERIVATIVES

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13-position with a 4-(α-L-oleandrosyl)-α-L-oleandrose group. The avermectin compounds and the instant derivatives thereof have a very high degree of anthelmintic and anti-parasitic activity.

The avermectin series of compounds isolated from the fermentation broth have the following structure:

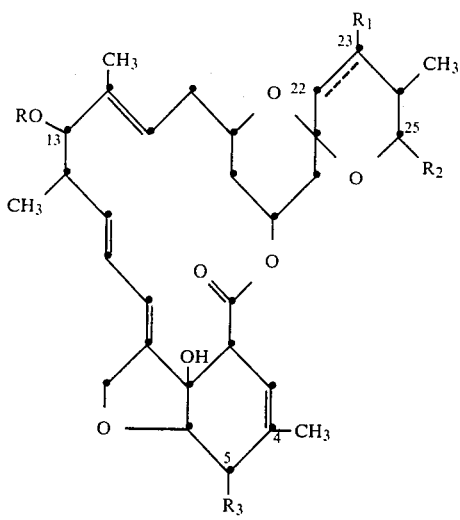

wherein R is the 4'-(α-l-oleandrosyl)-α-l-oleandrose group of the structure:

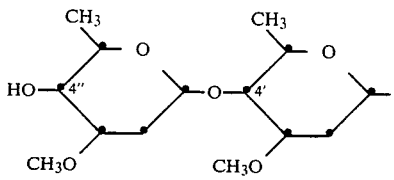

and wherein the broken line indicates a single or a double bond;

$R_1$ is hydroxy and is present only when said broken line indicates a single bond;

$R_2$ is iso-propyl or sec-butyl; and $R_3$ is methoxy or hydroxy.

There are eight different major avermectin natural product compounds and they are given the designations A1a, A1b, A2a, A2b, B1a, B1b, and B2a based upon the structure of the individual compounds.

In the foregoing structural formula, the individual avermectin compounds are as set forth below. (The R group is 4'(α-L-oleandrosyl)-α-L-oleandrose):

|     | $R_1$       | $R_2$      | $R_3$   |
|-----|-------------|------------|---------|
| A1a | Double Bond | sec-butyl  | —OCH₃   |
| A1b | Double Bond | iso-propyl | —OCH₃   |
| A2a | —OH         | sec-butyl  | —OCH₃   |
| A2B | —OH         | iso-propyl | —OCH₃   |
| B1a | Double Bond | sec-butyl  | —OH     |
| B1b | Double Bond | iso-propyl | —OH     |
| B2a | —OH         | sec-butyl  | —OH     |
| B2b | —OH         | iso-propyl | —OH     |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

In the isolation of the avermectin compounds from the fermentation broth, which serve as starting materials for the instant processes, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is often not practiced since the "b" compound is present only in a small amount, and the structural difference has negligible effect on the reaction processes and biological activities.

In particular it has been found that the starting materials for the compounds of this invention are very often prepared in a ratio of about 80% to 95% avermectin B1a or A1a and less than 20% avermectin B1b or A1b. Thus the preferred composition of this invention is one which contains not less than 80% of the "a" component and not more than 20% of the "b" component.

Milbemycin compounds are similar to the above avermectin compounds in that the 16-membered macrocyclic ring is present. However, such compounds have no substitution at the 13-position and have a methyl or ethyl group at the 25-position (the position the $R_2$ group is found in the above structure). To the extent that such milbemycin compounds can be oxidized to the 13-keto derivative and converted to the 13-imino and amino derivatives, they are to be construed as being within the ambit of this invention. Such milbemycin compounds and the fermentation conditions used to prepare them are described in U.S. Pat. No. 3,950,360. In addition, 13-deoxy-avermectin aglycones are prepared synthetically from the avermectin natural products and are disclosed in U.S. Pat. Nos. 4,171,314 and 4,173,571. Such compounds are very similar to the milbemycins differing from some of the milbemycins in having an isopropyl or sec butyl rather than a methyl or ethyl group at the 25-position.

SUMMARY OF THE INVENTION

The instant invention is concerned with certain derivatives of avermectin and milbemycin compounds wherein the 13-position hydroxy is oxidized to keto group which in turn is converted to the 13-imino and amino functions described below. Thus it is an object of the instant invention to describe such avermectin and milbemycin 13-keto, imino and amino compounds. A further object is to describe processes for the preparation of such compounds. A still further object is to describe the uses of such compounds as anti-parasitic agents. Still further objects will become apparent from a reading of the following description.

DESCRIPTION OF THE INVENTION

The compounds of the instant invention have the following structural formula.

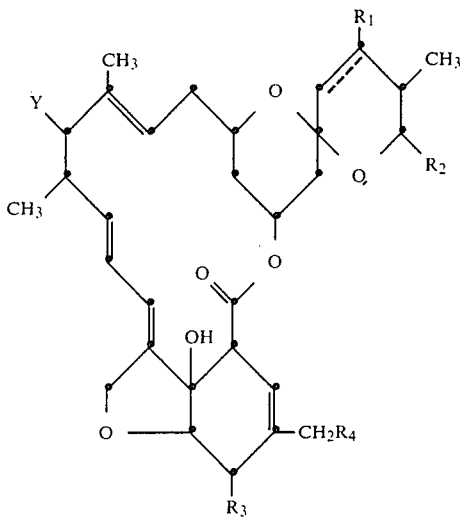

wherein the broken line indicates a single or double bond;
$R_1$ is H, —OH, loweralkanoyloxy, or =O provided that $R_1$ is present only when the broken line indicates a single bond;
$R_2$ is methyl, ethyl, isopropyl or sec-butyl;
$R_3$ is OH, loweralkoxy, or loweralkanoyloxy
$R_4$ is H, OH, or

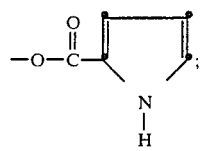

and
Y is =O, —$NH_2$, =NOH, =N—$NH_2$, =N—$NHC_6H_5$, =N—$NHCONH_2$, and =N—$NHCSNH_2$, =$NOR_5$ or —$NHR_5$ wherein $R_5$ is loweralkyl; and the trisubstituted silyl protected derivatives thereof.

The term "loweralkyl" when used in the instant application is intended to represent those alkyl groups either straight or branched chain which have from 1-5 carbon atoms. Examples of such alkyl groups are methyl, ethyl, propyl, iso-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propionyl, butyryl, valeryl, and the like.

One aspect of the preferred compounds of this invention is realized in the above structural formula when Y is =O, =NOH or =$NOCH_3$.

Specific examples of preferred compounds of the instant invention are:
13-oxo-22,23-dihydro avermectin B1a/B1b aglycone;
13-oxo-avermectin B1a/B1b aglycone;
13-oxo-milbemycin $α_1$;
13-oxo-milbemycin $α_3$;
13-oxo-avermectin B2a/B2b aglycone;
13,23-dioxoavermectin B2a/B2b aglycone;
13-deoxy-13-methoxyimino-22,23-dihydro avermectin B1a/B1b aglycone;
13-deoxy-13-methoximino-22,23-dihydro avermectin B2a/B2b aglycone.

The "b" compounds, those with a 25-iso-propyl group, are very difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture or when both compounds individually are intended, is sometimes done by referring to the B1 or B2 compounds or by separating the "a" compound from the "b" compound by a slash (/) such as B1a/B1b, B2a/B2b and the like.

The compounds of the instant invention are prepared by first oxidizing the compound wherein the 13-position substituent is hydroxy to the keto group, followed by treatment with the appropriate amine to prepare the imino or amino derivatives. The process is outlined in the following reaction scheme which, for clarity, show the partial structural formula including only the 10, 11, 12, 13, 14 and 15 carbon atoms of the above formula:

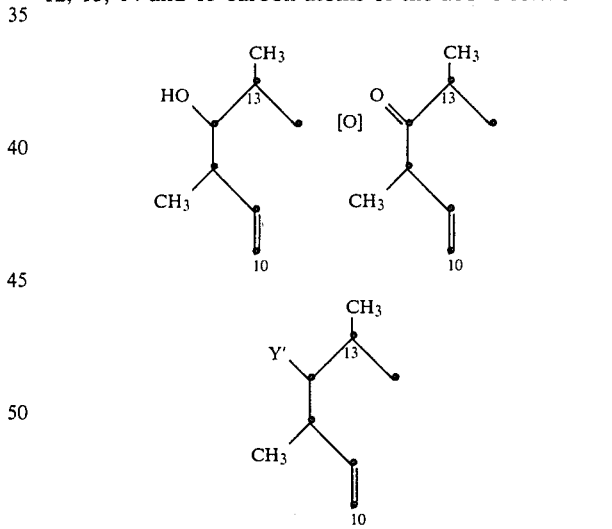

where the remainder of the molecule is as defined above and Y' is —$NH_2$, =NOH, =N—$NH_2$, =N—$NHC_6H_5$, =N—$NHCON_2$, =N—$NHCSNH_2$, =$NOR_5$ or —$NHR_5$ wherein $R_5$ is loweralkyl.

In the first step, the 13-hydroxy compound is oxidized to a ketone. Any oxidizing agent may be used which is capable of oxidizing a hydroxy to a ketone. Preferred oxidizing agents are compounds utilizing the higher oxidiation states of chromium such as chromium trioxide preferably in a complex such as with 3,5-dimethylpyrazole, pyridinium, dichromate, pyridinium chlorochromate and the like. Other preferred oxidizing agents are dimethyl sulfoxide with oxalyl chloride, dimethyl sulfoxide with trifluoroacetic anhydride, manganese dioxide and the like.

The reaction conditions used are those which, to one skilled in the art, are customary for such oxidations. Generally, the reaction is complete at about ambient temperature in ½ to 10 hours. Certain reagents may have more specialized conditions such as dimethylsulfoxide with oxalyl chloride which is generally carried out at from −80° to −40° C. This reaction involves the preparation of an intermediate which is decomposed releasing the product by the addition, while still cold, of a tertiary amine such as triethylamine. The reaction is completed by allowing it to rise to ambient temperature. The reaction is generally complete in about one hour, oftentimes less. The product is isolated using known techniques.

The imino derivatives are prepared from the keto derivatives in the second step of the above reaction scheme by reacting a primary amine with the keto compound in the presence of a base in an inert solvent. The base is preferably a tertiary amine such as pyridine or triethylamine and the solvent in any solvent which will not react with any of the reactants. Inert solvents such as methanol, ethanol, isopropanol, dimethoxyethane, N,N-dimethylformamide, and the like are preferred. The reaction is generally carried out at the reflux temperature of the reaction mixture and is generally complete in from 1 to 10 hours. The product is isolated using techniques known to those skilled in the art.

To prepare the 13-amino compounds, the 13-keto compound is reductively aminated to prepare the unsubstituted amino compound. The reaction is carried out in an inert solvent such as methanol at from −25° to +25° C. using ammonium salts and sodium cyanoborohydride as the aminating and reducing reagents. The reaction is complete in from 15 minutes to 2 hours and the product 13-deoxy-13-amino compound is isolated using known techniques. Suitable ammonium salts are the acetate, propionate and benzoate. The acetate is preferred.

As a variation to the foregoing amination reaction, methyl ammonium salts could be used in place of the ammonium salts to prepare the monomethyl substituted compound. The same reagents, salts and reaction conditions as described above can be used for such a reaction. Other alkyl ammonium salts can also be used in this process.

PREPARATION OF STARTING MATERIALS

The ultimate starting materials for the compounds of this invention are the avermectin and milbemycin fermentation products defined above. Thus it is apparent that additional reactions are required to prepare many of the starting materials for the instant compounds. Specifically, reactions are carried out at the 4a, 5, 13, 22, and 23-positions. It is generally preferred to prepare whatever substituents are required at these positions before carrying out the reaction to introduce the 13-position groups on the substrate. Such a procedure generally avoids undesirable side reactions. This technique is not required, however, and if desired, other sequences may be used. In addition, it is often necessary to protect certain reactive hydroxy groups where reaction with the above reagents is not desired. With the appropriate positions protected, the above reactions may be carried out without affecting the remainder of the molecule. Subsequent to any of the above described reactions the protecting group may be removed and the unprotected product isolated. The protecting group employed is ideally one which may be readily synthesized, will not be affected by the reaction with the oxidation reagents and the amines and may be readily removed without affecting any other functions of the molecule. It is noted that the instant protected compounds are novel and have considerable antiparasitic activity. They are included within the ambit of the instant invention. One preferred type of protecting group for the avermectin and milbemycin type of molecule is the tri-substituted silyl group, preferably the trialkyl silyl group. One especially preferred example is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions. If it is desired to protect the 23-hydroxy group a 4", 5,23-tri(phenoxyacetyl) derivative can be prepared. Basic hydrolysis will leave the highly hindered 23-O-substituent but will hydrolize the 5-and 4"-O-phenoxy acetyl groups leaving them available for reaction. The 5-position may be selectively protected as described above with t-butyl-dimethylsilyl, and the 4" group may be reacted.

The silyl group may be removed after the other contemplated reactions may be carried out. The silyl group or groups are removed by stirring the silyl compound in methanol catalyzed by a catalytic amount of an acid, preferably a sulfonic acid such as p-toluene sulfonic acid. The reaction is complete in about 1 to 12 hours at from 0° to 50° C.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the 1-series of compounds. Thus in the "1" series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

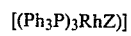

wherein
Ph is phenyl and Z is halogen. The reduction procedure is completely described in U.S. Pat. No. 4,199,569 to Chabala et al.

All of the starting materials for the compounds of this invention require the removal of both of the α-L-oleandrosyl moieties (described in U.S. Pat. No. 4,206,205 to Mrozik et al.). The selective acylation of the susceptible hydroxy groups is described in U.S. Pat. No. 4,201,861 to Mrozik et al.

The reaction conditions which are generally applicable to the preparation of the aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 1 to 10% by volume. The reaction mixture is generally stirred at about 20°–40° C., preferably at room temperature, for from 6 to 24 hours. The products are isolated, and mixtures are separated by techniques such as column, thin layer, preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the aglycone of the avermectin compounds or of the hydrogenated avermectin compounds utilizes a different solvent system. For the preparation of the aglycone, 1% acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acids listed above are appropriate for this process, and again sulfuric acid is the preferred acid.

The acylated compounds are prepared using acylation techniques in which the reaction conditions will vary, depending upon the reactivity of the hydroxy group being acylated. Where there is more than one hydroxy group to be acylated, different reaction conditions are employed to minimize the formation of mixtures. The acylation reactions are described completely in U.S. Pat. No. 4,201,861 to Mrozik et al.

The acylation reagents employed are generally the halide, preferably the chloride, of the above loweralkanoyl groups. That is the loweralkanoyl halide reagent is generally employed.

In addition, the acylation reagent could be in the form of the anhydride or of the halo formate. In the case of reactions carried out with the halide reagents, it is often advantageous to include in the reaction mixture a basic compound capable of reacting with and neutralizing the hydrogen halide which is liberated during the course of the reaction. Tertiary amines are preferred such as triethylamine, pyridine, dimethylamino pyridine, diisopropyl ethylamine and the like. The basic compound is required in equimolar amounts relative to the numbered moles of hydrogen halide being liberated, however excess amounts, even using the basic compound as a solvent, are not detrimental. Many other acylation procedures are known in the art and may be used to prepare the above described acylated avermectin and milbemycin compounds.

The A2 compounds have two available hydroxy groups, the 13- and the 23-positions. The 13-position is to be oxidized thus the 23-hydroxy group must be protected by selective acylation. This is more readily accomplished by selective hydrolysis of the diacyl compound.

The 13-monoacyl compound will be prepared by using the reaction conditions described above for the A1 compound. Since the 23-hydroxy is less reactive than the 13-position, mild reaction conditions (0° C.) will afford predominantly the 13-monoacyl compound which is the undesired product. Heating the reaction mixture at from room temperature to 100° C. for from 1 to 24 hours will produce the 13, 23-diacyl compound. Since the 23-monoacyl compound is desired, the diacyl compound is treated with aqueous base, such as sodium hydroxide, at room temperature for from 1 to 24 hours. The 13 acyl group will be hydrolyzed leaving the 23 monoacyl compound.

The B1 and 22,23-dihydro B1 compounds have 2 available hydroxy groups: at the 13- and the 5-positions. However, the two hydroxy groups have different reactivities. The 5-hydroxy group can be protected specifically by the preparation of the 5-O-tert-butyldimethylsilyl or other trisubstituted silyl derivative as described by Mrozik et al. in *Tetrahedron Letters* 24 pg 5333–5336 (1983).

The B2 compounds have three hydroxy groups available for substitution: the 13, 5 and 23 positions. In order to prepare the protected starting materials required for the selective oxidation of the 13-hydroxy group, the B2 compounds are first converted selectively to the corresponding 5-O-tert-butyldimethylsilyl derivative and then further treated as described above for the A2 compounds containing an unreactive 5-methoxy group.

The 4a-hydroxy compounds are prepared best by oxidizing a 4-methyl compound containing the desired substitutions at the 13-position and at other positions in the molecule using procedures described in U.S. patent application Ser. No. 404,960, now U.S. Pat. No. 4,457,920, incorporated herein by reference. Such procedure specifically oxidizes a vinylic methyl group to the corresponding allylic alcohol. It was found and described in the above application that tert-butyl hydroperoxide, with selenium dioxide as catalyst, specifically transforms the 4-methyl group of avermectins and milbemycins into a 4a-hydroxy compound.

The preferred process involves treating the 4-methyl compound with t-butyl hydroperoxide in the presence of a catalytic amount of selenium dioxide. Under these conditions the selenium dioxide actually oxidizes the 4-methyl to a 4a-hydroxy methyl and is itself reduced in the process. The t-butyl hydroperoxide oxidizes the reduced selenium compounds back to selenium dioxide for further oxidation of the molecule. In this way only a small, catalytic amount of the selenium dioxide is required.

The reaction is carried out in an inert solvent; one not susceptible to oxidation. Methylene chloride is preferred, however, ethyl acetate, tetrahydrofuran and the like may also be employed. The reaction temperature may be from 0° to 50° C., however, reaction at room temperature is preferred. Under these conditions the reaction is generally complete in from 1–48 hours, however, under the preferred condition the reaction is generally complete in about 24 hours.

The necessary starting materials for the preparation of the 13-oxo- and 13-imino milbemycin derivatives, which do not have a 13-hydroxy group, are obtained first by introduction of said hydroxy group into the molecule as described in U.S. Pat. No. 4,134,973. The thus obtained 13-hydroxy milbemycins are then reacted as described herein for the avermectin aglycones.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly Musca domestica.

The compounds are also useful against insect pests of stored grains such as Tribolium sp., Tenebrio sp. and of agricultural plants such as2spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

In the following examples, the various starting materials therefor are avermectin compounds, derivatives of avermectin compounds or milbemycin compounds. The avermectin compounds and the preparation and isolation thereof from fermentation broths are described in U.S. Pat. No. 4,310,519 issued Jan. 12, 1982. The selective 22,23-dihydro derivatives of avermectin compounds are described in U.S. Pat. No. 4,199,569 issued Apr. 22, 1980. The aglycone and monosaccharide derivatives of avermectin compounds are described in U.S. Pat. No. 4,206,205 issued Jan. 3, 1980. The 13-hydroxy milbemycin derivatives are prepared as described in U.S. Pat. No. 4,134,973.

EXAMPLE 1A

23-O-t-Butyldimethylsilyl avermectin A2a/A2b aglycone

200 Mg of avermectin A2a/A2b in 2.4 ml of dry dimethyl formamide was combined with 133 mg of imidazole and stirred until a solution resulted. The 146 mg of t-butyldimethylsilylchloride was added and the reaction mixture was stirred at room temperature overnight, and allowed to stand for 6 more hours. The reaction mixture was diluted with ether and washed 5 times with water and the water layers washed with ether. The combined ether layers were washed with saturated sodium chloride, dried and evaporated to dryness in vacuo affording 340 mg of an oil. The oil was dissolved in methylene chloride and placed on two 2000$\mu$ silica gel preparative layers plates and eluted with 5% tetrahydrofuran and 0.5% ethanol in methylene chloride. Of the 3 major bands, the middle one contained 113.2 mg of material identified as 3-O-t-butyldimethylsilyl avermectin A2a/A2b aglycone.

EXAMPLE 1B

23-O-t-butyldimethylsilyl-13-oxo-avermectin A2a/A2b aglycone

58 Mg of 3,5-dimethylpyrazole and 60 mg of chromium trioxide were combined in a sealed flask under nitrogen. 2.0 ml of anhydrous methylene chloride was added and the mixture stirred for 15 minutes at room temperature to obtain a solution. A solution of 100 mg of 23-O-tertiarybutyldimethylsilyl avermectin A2a/A2b aglycone in 2.0 ml of anhydrous methylene chloride was added and the mixture stirred at room temperature for 30 minutes. The reaction mixture was evaporated to dryness under a stream of dry nitrogen and the residue was extracted 3 times with 8 ml each of ether and the combined ether extracts are evaporated in vacuo affording 78 mg of a brown glass which was placed on a single 1000$\mu$ silica gel plate and developed with a mixture of 94.5:5:0.5 mixture of methylene chloride:tetrahydrofuran:ethanol affording 45 mg of a colorless glass which nuclear magnetic resonance and mass spectrometry revealed to be 23-O-tertiarybutyldimethylsilyl-13-oxo-avermectin A2a/A2b aglycone.

EXAMPLE 2

13-Oxo-avermectin A2a/A2b aglycone

10 Mg of the product recovered from Example 1 in 1.0 ml of a 1% para-toluenesulfonic acid dihydrate solution in methanol was stirred at room temperature for 2½ hours. To the mixture was added aqueous saturated sodium bicarbonate solution which was extracted with ether and the ether extracts washed with water and dried over magnesium sulfate and concentrated to dryness under a stream of dry nitrogen affording a colorless oil. The oil was placed on a 250μ silica gel plate and diluted with a 95:5:0.5 mixture of methylene chloride, tetrahydrofuran and ethanol affording a single band of a colorless oil giving 5.8 mg which was shown by mass spectrometry and nuclear magnetic resonance to be 13-oxo-avermectin A2a/A2b aglycone.

EXAMPLE 3

22,23-Dihydro-13-oxo-avermectin B1a/B1b aglycone

Following the procedure of Example 2, utilizing 20 mg of 22,23-dihydro-13-oxo-5-O-t-butyl dimethylsilyl-avermectin B1a/B1b aglycone there was obtained 22,23-dihydro-13-oxo-avermectin B1a/B1b aglycone.

EXAMPLE 4

22,23-Dihydro-5-O-t-butyldimethylsilyl-13-oxoavermectin B1a/B1b aglycone

To a solution containing 38.4 μl of oxalyl chloride in 1.0 ml of dry methylene chloride at −60° C. was added 62 μl of dry dimethylsulfoxide dissolved in 0.4 ml of dry methylene chloride. The evolution of a gas was observed while the mixture was stirred at −60° C. for 2 minutes. With a syringe was added 140 mg of 22,23-dihydro-5-O-t-butyldimethylsilyl avermectin B1a/B1b aglycone in 1.2 ml of dry methylene chloride over a period of 5 minutes while maintaining the temperature at −60° C. The reaction mixture was stirred at this temperature for 30 minutes whereupon 280 μl of dry triethylamine was added and the mixture stirred for 5 minutes. The cooling bath was removed and the reaction mixture was allowed to come to ambient temperature and stirred for 30 to 40 minutes. Water was added to the reaction mixture and the mixture extracted 4 times with ether and methylene chloride and the combined organic layers washed 6 times with water, dried over anhydrous sodium sulfate and evaporated to dryness in vacuo. The residue was placed on three 1000μ silica gel plates, and the plates were developed with a 5% methanol in methylene chloride solution. The product was removed from the silica gel and identified by nuclear magnetic resonance and mass spectrometry as 22,23-dihydro-5-O-t-butyldimethylsilyl-13-oxoavermectin B1a/B1b aglycone.

EXAMPLE 5

22,23-Dihydro-13-oxo-avermectin B1a/B1b aglycone semicarbazone

Following the procedure of Example 2, using 150 mg of 22,23-dihydro-5-O-t-butyldimethylsilyl-13-oxo-avermectin B1a/B1b aglycone semicarbazone and 13 ml of a 0.5% para-toluene sulfonic acid solution in methanol, there is obtained 22,23-dihydro-13-oxo-avermectin B1a/B1b aglycone semicarbazone.

EXAMPLE 6

22,23-Dihydro-5-O-t-butyldimethylsilyl-13-oxoavermectin B1a/B1b aglycone semicarbazone In a round-bottom flask under a stream of nitrogen was combined 500 mg of 22,23-dihydro-5-O-t-butyl-dimethylsilyl-13-oxo-avermectin B1a/B1b aglycone, 400 mg of semicarbazide hydrochloride and 4 ml of pyrridine. The reaction mixture was stirred at reflux for 4 hours, cooled and evaporated to dryness in vacuo. The residue was extracted with methylene chloride and the solution was again concentrated in vacuo to give 750 mg of crude product. This material was placed on a silica gel column, eluted with a mixture of 1% methanol and methylene chloride; 20 ml fractions were taken affording 242.5 mg from combined fractions 17–24 and 209.3 mg from fractions 25–40. The remaining fractions were discarded. Nuclear magnetic resonance and mass spectrometry showed both fractions to contain 22,23-dihydro-5-O-t-butyldimethylsilyl-13-oxo-avermectin B1a/B1b aglycone semicarbazone.

EXAMPLE 7

22,23-Dihydro-13-oxo-avermectin B1a/B1b aglycone thiosemicarbazone.

Following the procedure of Example 2, using 55 mg of 22,23-dihydro-5-O-t-butyldimethylsilyl-13-oxo-avermectin B1a/B1b aglycone thiosemicarbazone and 7.5 ml of 0.5% para-toluenesulfonic acid in methanol afforded 22,23-dihydro-13-oxo-avermectin B1a/B1b aglycone thiosemicarbazone.

EXAMPLE 8

22,23-Dihydro-5-O-t-butyldimethylsilyl-13-oxoavermectin B1a/B1b aglycone thiosemicarbazone 48.5 Mg (0.07 mmoles) of 22,23-dihydro-5-O-t-butyl-dimethylsilyl-13-oxo-avermectin B1a/B1b aglycone, 91 mg (1.0 mmoles) of thiosemicarbazide, 3 drops of glacial acetic acid and 2.0 ml of ethanol were combined and refluxed under a stream of nitrogen for 20 hours. The reaction mixture was evaporated in vacuo, the residue triturated with methylene chloride, the organic layer filtered and the filtrate concentrated in vacuo. The residue was purified on a column of silica gel eluting with 1% methanol in methylene chloride taking 6.0 ml fractions as follows: fractions 2–8 were discarded, fractions 8–14 contained starting material and fractions 15–17 contained product weighing 28 mg. The product fractions were further purified on a 500∞ preparative chromatography plate using a mixture of 5% methanol in methylene chloride for development. Repeated solvent passes afforded 21.2 mg of product which nuclear magnetic resonance and mass spectrometry identified as 22,23-dihydro-5-O-t-butyl-dimethylsilyl-13-oxo-avermectin B1a/B1b aglycone thiosemicarbazone.

EXAMPLE 9

22,23-Dihydro-5-O-t-butyldimethylsilyl 13-deoxy-13-methoxyiminoavermectin B1a/B1b aglycone 105 Mg of 22,23-dihydro-5-O-t-butyldimethysilyl-13-oxo-avermectin B1a/B1b aglycone, 125 mg of methoxyimine hydrochloride, 0.5 ml of pyrridine and 5 ml of ethanol were combined and refluxed under a blanket of nitrogen for 5 hours and then allowed to stand overnight at room temperature. The reaction mixture was evaporated to dryness in vacuo and the residue triturated with methylene chloride and the organic layers filtered and evaporated to dryness in vacuo. The residue was purified on two 500μ preparative layer silica gel chromatography plates eluting twice with a 30 to 70 mixture of ethyl ether and petroleum ether and repeating the elutions with a mixture of 5% methanol in methylene chloride 6 times. Two product bands were removed from the plate and placed separately on a new 500μ silica gel plate eluting with a 6 to 94 mixture of ether and petroleum ether, then a 15% ether and petroleum ether mixture to afford 26 mg and 28 mg respectively of two isomeric products identified by nuclear magnetic resonance and mass spectrometry as 22,23-dihydro-5-O-t-butyldimethylsilyl-13-methoximino-avermectin B1a/B1b aglycones.

EXAMPLE 10

22,23-Dihydro 13-deoxy-13-methoximino-avermectin B1a/B1b aglycone-isomer A

Following the procedure of Example 2, using 23 mg of 22,23-dihydro-5-O-t-butyldimethylsilyl-13-methoximino-avermectin B1a/B1b aglycone in 3.5 ml of 0.5% peritoluenesulfonic acid in methanol there was obtained 22.5 mg of 22,23-dihydro-13-methoximino-avermectin B1a/B1b aglycone, isomer A.

EXAMPLE 11

22,23-Dihydro 13-deoxy-13-methoximino-avermectin B1a/B1b aglycone-isomer B

The procedure of Example 10 was repeated using 24 mg of 22,23-dihydro-5-O-t-butyldimethylsilyl-13-methoximino-avermectin B1a/B1b aglyconeisomer B in 5.0 ml of 0.5% para-toluenesulfonic acid in methanol to afford 17.3 mg of the second isomer of 22,23-dihydro-13-methoximino-avermectin B1a/B1b aglycone.

EXAMPLE 12

13-Oxo avermectin A1a/A1b

Following the procedure of Example 4 using 38 μl oxalyl chloride, 1.0 ml of methylene chloride, 62 μl dimethyl sulfoxide in 0.4 ml of methylene chloride 120 mg (0.2 mmole) of avermectin A1a/A1b aglycone dissolved in 1.2 ml of methylene chloride, and 280 μl of triethylamine, gives after chromatographic purification 13-oxo avermectin A1a/A1b.

EXAMPLE 13

4a-Hydroxy-13-oxo-22,23-dihydro avermectin B1a/B1b Aglycone

A mixture of 5.5 mg of selenium dioxide, 0.3 ml of methylene chloride and 22 μl of t-butylhydroperoxide is stirred at room temperature for 30 minutes. Then a solution of 60 mg of 13-oxo-22,23-dihydro avermectin B1a/B1b aglycone in 0.2 ml of methylene chloride is added and the mixture is stirred at room temperature for 24 hours. The mixture is diluted with ether for work up and washed with water. The residue obtained by concentration of the organic phase is purified by chromatography on a reverse phase column using aqueous methanol as the solvent. The structure of the major product is determined by NMR and mass spectra as 4a-hydroxy-13-oxo-22,23-dihydroavermectin B1a/B1b aglycone.

EXAMPLE 14

13-Oxo milbemycin α4

Following the procedure of Example 4 using a solution of 20 μl of oxalyl-chloride, 30 μl of dimethyl sulfoxide in 0.7 ml of methylene chloride and 57 mg of 13-hydroxy milbemycin α4 (obtained according to the procedure described in U.S. Pat. No. 4,134,973) dissolved in 0.6 ml of methylene chloride followed by 140 μl of triethylamine one obtains 13-oxo milbemycin 60 4.

EXAMPLE 15

13-Amino 13-deoxy-5-O-t-butyldimethylsilyl 22,23-dihydro avermectin B1a/B1b aglycone 699 Mg of 13-oxo-5-O-t-butyldimethylsilyl-22,23-dihydro avermectin B1a/B1b aglycone, 771 mg of ammonium acetate, and 700 mg of 3A powdered molecular seive were combined in 15 ml of dry methanol and stirred at room temperature for 4 hours under a blanket of dry nitrogen. Then 57 mg of sodium cyano borohydride dissolved in 2.5 ml of dry methanol was added dropwise. The mixture was then stirred at room temperature for 48 hours. The reaction mixture was taken up in 100 ml of methylene chloride and 50 ml of aqueous sodium bicarbonate. The layers were separated and the aqueous layer washed with methylene chloride. The combined organic layers were dried over sodium sulfate and evaporated to dryness affording 647 mg of a crude product as yellow foam. Chromatography on a silica gel column with a mixture of methylene chloride-methanol-water =99:1:0.1 gave 217 mg of pure product which nuclear magnetic resonance identified as 13-amino 13-deoxy-5-O-t-butyldimethylsilyl-22,23-dihydro avermectin B1a/B1b aglycone.

EXAMPLE 16

13-Amino 13-deoxy-22,23-dihydro avermectin B1a/B1b aglycone

Following the procedure of Example 2 using 1% para-toluenesulfonic acid in methanol there was obtained from 40 mg of the product of Example 15, 29 mg of 13-amino 13-deoxy 22,23-dihydro avermectin B1a/B1b aglycone.

What is claimed is:

1. A compound having the formula:

III wherein the broken line indicats a single or a double bond; wherein $R_1$ is H,—OH, loweralkanoyloxy, or =O provided that $R_1$ is present only when the broken line indicates a single bond;

$R_2$ is methyl, ethyl, iso-propyl or sec-butyl;

$R_3$ is OH, loweralkoxy or loweralkanoyloxy;

$R_4$ is H, OH, or

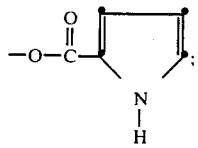

and

Y is =O, —NH$_2$, =NOH, =N—NH$_2$, =N—N-H—C$_6$H$_5$, =N—NH—CONH$_2$, =N—N-H—CSNH$_2$, =NOR$_5$ or —NHR$_5$ wherein R$_5$ is loweralkyl; or a trialkyl silyl protected derivative thereof.

2. The compounds of claim 1 wherein Y is: =O, =NOH or =NOCH$_3$.

3. The compound of claim 2 which is 13-oxo-22,23-dihydro avermectin B1a and/or B1b aglycone.

4. The compound of claim 2 which is 13-oxo-avermectin B1a and/or B1b aglycone.

5. The compound of claim 2 which is 13-oxo-milbemycin α$_1$.

6. The compound of claim 2 which is 13-oxo-milbemycin α$_3$.

7. The compound of claim 2 which is 13-oxo-avermectin B2a and/or B2b aglycone.

8. The compound of claim 2 which is 13,23-dioxo avermectin B2a and/or B2b aglycone.

9. The compound of claim 2 which is 13-deoxy-13-methoximino-22,23-dihydro avermectin B1a and/or B1b aglycone.

10. The compound of claim 2 which is 13-deoxy-13-methoximino avermectin B1a and/or B1b aglycone.

11. The compound of claim 1 which is 13-amino-13-deoxy-22,23-dihydro avermectin B1a and/or B1b aglycone.

12. A method for the treatment of parasitic infections which comprises administering to an animal infected with parasites an effective amount of a compound of claim 1.

13. A composition useful for treating animals infected with parasites which comprises an inert carrier and an effective amount of a compound of claim 1.

* * * * *